(12) United States Patent
Zappi et al.

(10) Patent No.: US 12,194,188 B2
(45) Date of Patent: Jan. 14, 2025

(54) RACK FOR TREATMENT OF RESPIRATORY MASKS

(71) Applicant: University of Louisiana at Lafayette, Lafayette, LA (US)

(72) Inventors: Mark E. Zappi, Lafayette, LA (US); William Holmes, Lafayette, LA (US); Andrei Chistoserdov, Lafayette, LA (US); Wayne Sharp, Lafayette, LA (US); Alex Zappi, Lafayette, LA (US); Rafael Hernandez, Lafayette, LA (US); William Chirdon, Lafayette, LA (US); Don Begneaud, Lafayette, LA (US); Thomas Broussard, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 502 days.

(21) Appl. No.: 17/219,930

(22) Filed: Apr. 1, 2021

(65) Prior Publication Data

US 2021/0308312 A1    Oct. 7, 2021

Related U.S. Application Data

(60) Provisional application No. 63/004,591, filed on Apr. 3, 2020.

(51) Int. Cl.
| | |
|---|---|
| *A61L 2/26* | (2006.01) |
| *A47B 81/00* | (2006.01) |
| *A61L 2/10* | (2006.01) |
| *A61L 2/20* | (2006.01) |
| *A61L 101/02* | (2006.01) |

(52) U.S. Cl.
CPC ............... *A61L 2/26* (2013.01); *A47B 81/00* (2013.01); *A61L 2/10* (2013.01); *A61L 2/202* (2013.01); *A61L 2/208* (2013.01); *A61L 2101/02* (2020.08); *A61L 2202/26* (2013.01)

(58) Field of Classification Search
CPC ... A61L 2/26; A61L 2/10; A61L 2/202; A61L 2/208; A61L 2101/02; A61L 2202/26; A47B 81/00
See application file for complete search history.

(56) References Cited

U.S. PATENT DOCUMENTS

| | | | | |
|---|---|---|---|---|
| 896,708 | A * | 8/1908 | Bruce | A47J 27/04 126/261 |
| 1,091,907 | A * | 3/1914 | Benners | B65D 11/1873 220/4.28 |

(Continued)

FOREIGN PATENT DOCUMENTS

| | | | | |
|---|---|---|---|---|
| FR | 2763245 A1 * | 11/1998 | | A61L 2/07 |
| NL | 1004306 C1 * | 4/1998 | | A61L 2/07 |
| WO | WO-2019112526 A1 * | 6/2019 | | A61B 50/30 |

*Primary Examiner* — Stanton L Krycinski
(74) *Attorney, Agent, or Firm* — Kean Miller LLP; Jessica C. Engler; Brian J. Servé

(57) ABSTRACT

A rack for sanitizing or cleaning medical or personal protective equipment is claimed herein. The rack has at least two stringers that run the length of the rack. The rack has at least two vertical grates that are spaced apart from each other along the stringers. The spacing between the grates will be sufficient such that a standard respiratory mask (e.g. N95) may be placed between two adjacent grates and be held in a vertical orientation.

5 Claims, 1 Drawing Sheet

(56) References Cited

U.S. PATENT DOCUMENTS

| | | | | | |
|---|---|---|---|---|---|
| 1,951,099 | A | * | 3/1934 | Meyerson | A61L 2/06 422/302 |
| 2,552,983 | A | * | 5/1951 | Lee | A61L 2/26 211/74 |
| 3,347,404 | A | * | 10/1967 | McIntyre | A47J 27/122 220/759 |
| 3,380,592 | A | * | 4/1968 | Arnold | B65D 83/005 426/115 |
| 3,904,362 | A | * | 9/1975 | DiPaolo | A61L 2/26 206/209 |
| 4,179,040 | A | * | 12/1979 | Bateman | A47J 47/02 220/660 |
| D257,201 | S | * | 10/1980 | Croyle | D7/547 |
| 4,561,547 | A | * | 12/1985 | Estwanik, III | A47B 81/00 211/113 |
| 4,836,392 | A | * | 6/1989 | Constantino | A61J 11/00 211/41.9 |
| 5,053,207 | A | * | 10/1991 | Lervick | A61L 2/18 422/301 |
| 5,082,135 | A | * | 1/1992 | DeCoster | B65D 83/005 206/804 |
| D333,757 | S | * | 3/1993 | DeCoster | D7/669 |
| 5,195,424 | A | * | 3/1993 | Guajaca | A47J 36/22 126/369 |
| D339,266 | S | * | 9/1993 | Lockett | D7/354 |
| 5,356,206 | A | * | 10/1994 | Van Valkenburgh | A47B 57/06 312/317.1 |
| 5,402,810 | A | * | 4/1995 | Donley | B08B 3/044 134/200 |
| D364,929 | S | * | 12/1995 | Bigler | B65D 83/005 D6/677.1 |
| 6,213,777 | B1 | * | 4/2001 | Seitzinger | A61C 17/036 433/229 |
| 6,390,104 | B1 | * | 5/2002 | Gagnon | A61C 17/036 134/107 |
| D615,355 | S | * | 5/2010 | Viahos | A47B 81/00 D7/409 |
| 8,182,760 | B2 | * | 5/2012 | Lee | A61L 2/07 422/26 |
| D662,215 | S | * | 6/2012 | Schofield | A61L 2/26 D24/217 |
| D662,789 | S | * | 7/2012 | Rowan | B65D 83/005 D7/667 |
| 8,418,872 | B2 | * | 4/2013 | Smith | B65D 55/02 220/784 |
| 8,596,782 | B2 | * | 12/2013 | Matsuzawa | A61L 2/18 351/159.33 |
| 8,685,318 | B2 | * | 4/2014 | Collard | A61L 2/24 422/1 |
| 9,358,084 | B2 | * | 6/2016 | Prewitt | A61C 17/036 |
| 9,427,484 | B1 | * | 8/2016 | Alvarado | D06B 23/18 |
| 9,687,124 | B1 | * | 6/2017 | Riggs, Jr. | A47B 55/02 |
| 9,687,575 | B2 | * | 6/2017 | Farren | A61L 2/10 |
| 9,737,625 | B2 | * | 8/2017 | Patterson, Jr. | A61L 2/14 |
| 10,827,659 | B2 | * | 11/2020 | Nguyen | A61L 2/26 |
| 2011/0020193 | A1 | * | 1/2011 | Lee | A61L 2/07 422/292 |
| 2018/0071420 | A1 | * | 3/2018 | Bestel | A61L 2/26 |
| 2021/0299304 | A1 | * | 9/2021 | Concannon | A61L 2/26 |

* cited by examiner

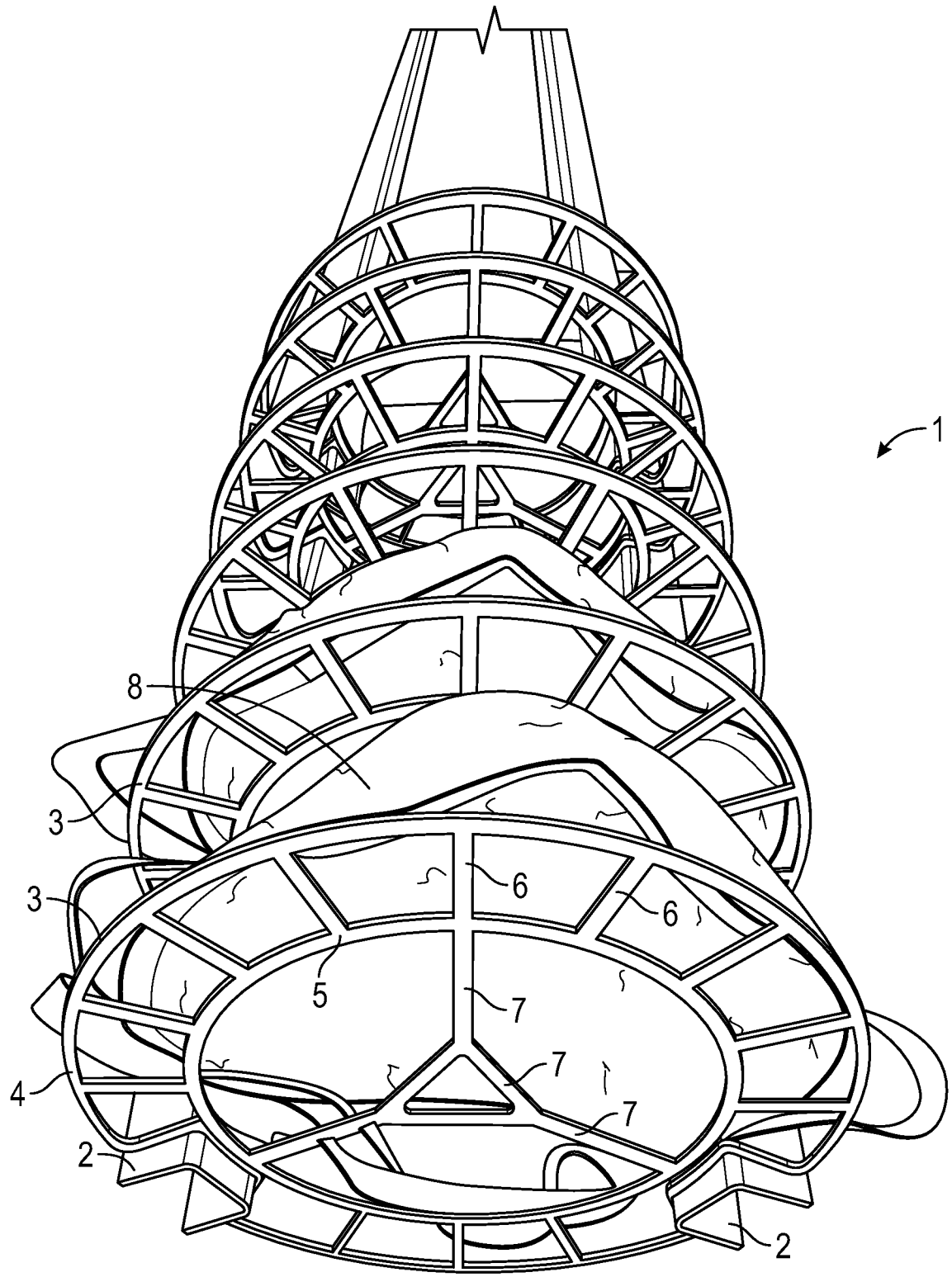

RACK FOR TREATMENT OF RESPIRATORY MASKS

CROSS REFERENCE TO RELATED APPLICATIONS

The applications claims the benefit of and priority to U.S. Provisional Application No. 63/004,591 entitled, "Rack for Treatment of Respiratory Masks" and filed on Apr. 3, 2020.

STATEMENT REGARDING FEDERALLY SPONSORED RESEARCH OR DEVELOPMENT

Not Applicable.

REFERENCE TO A "SEQUENCE LISTING," A TABLE, OR A COMPUTER PROGRAM

Not Applicable.

DESCRIPTION OF THE DRAWINGS

The drawing constitutes a part of this specification and includes an exemplary embodiment of the Rack for Treatment of Respiratory Masks, which may be embodied in various forms. It is to be understood that in some instances, various aspects of the invention may be shown exaggerated or enlarged to facilitate an understanding of the invention. Therefore the drawing may not be to scale.

FIG. 1 depicts one embodiment of the device.

BACKGROUND

Medical personnel, first responders, and other personnel rely on Personal Protective Equipment to protect them from infection when performing their jobs. Personal Protective Equipment (PPE) may include respiratory masks, hoods, gowns, disposable scrub sets, HazMat (Hazardous Material) suits, or other items that serve as a barrier against viruses, bacteria, fungi, or other organisms and substances that can cause illness, such as blood, urine, and saliva. Adequate supplies of PPE will be critical when a particular region is faced with an epidemic or pandemic.

Normally, used PPE items are thrown out as waste and cannot be reused. While normal levels of PPE supplies may initially be adequate in the face of an outbreak of communicable diseases, as the pandemic spreads those supplies will likely be exhausted.

The invention described herein provides a device that may be used for treating used respiratory masks so that they can be used again. While the description and claims described herein focus on respiratory masks, those skilled in the art will find other applications for the device.

DETAILED DESCRIPTION

With reference to the preferred embodiment of FIG. 1, the rack 1 has at least two stringers 2 that run the length of the rack. The rack 1 will have at least two vertical grates 3 that are spaced apart from each other along the stringers 2. The spacing between the grates 3 will be sufficient such that a standard respiratory mask 8 (e.g. N95) may be placed between two adjacent grates and be held in a vertical orientation (as if being worn by a person).

As shown in FIG. 1, each grate 3 has an outer ring 4, an inner ring 5, radial ring members 6 connecting the two rings, and center connectors 7 interior of the inner ring.

The overall shape of the grate 3 is circular so that the rack 1 may be adapted for use in a tubular shaped treatment chamber (not shown). However, the structure of the grates 3 can be of any configuration that connects the stringers 2 and allows gas to flow through the grates 3.

While the embodiment in FIG. 1 has two stringers 2, the rack 1 may be configured with three or more stringers. The rack 1 may also have a single wider stringer. However, it is preferable that the rack have two or more narrow stringers so as to promote the flow of the disinfecting gas through and around the masks.

In one or more embodiments the component parts are connected via a weld. In other embodiments, the rack may comprise one or more integrated pieces.

The treatment device may use ozone, the vapor form of hydrogen peroxide, or other gases that are known to disinfect the mask materials. Thus, the rack 1 and component parts are configured so as to hold the masks 8 upright. In one or more embodiments, the cupped part of a concave mask 8 is facing the incoming gas stream to maximize gas contact with the pores of the materials being treated.

While the embodiment depicted has a circular cross-section so as to be adapted for use in a tubular treatment chamber, those skilled in the art may provide other cross-section shapes adapted to match to shapes of other treatment chambers. The rack 1 is proportioned so that it easy to insert and withdraw from the treatment chamber. In a particularly preferred embodiment, the rack may also include rollers to facilitate movement in and out of the treatment chamber.

While the preferred embodiment of FIG. 1 is on a scale for treatment of masks, the size of the rack may be scaled to a very large application (e.g. HazMat suits). Additionally, the rack may be used for decontamination of medical devices, medical instruments, lab equipment, emergency equipment, or any other item needed decontamination.

The rack may be used for the disinfecting of masks and other PPE items of pathogens and other hazards, including but not limited to viruses (including the corona virus or COVID 19 virus), bacteria, and fungi.

The rack may also be used in treatment chambers that can be filled with ozonated water or other liquids to use a wet disinfection mode. However, for many PPE items (e.g. N95 masks), wet disinfection will not be suitable.

In another embodiment, the reactor can be configured so that it resembles a sealed hanging clothes closet/box to allow for disinfection of hanging PPE. The rack can be modified to hold open gloves set into the reactor for disinfection. It will be obvious to those skilled in the art to disinfect other medical devices using both reactor designs-those using ozone alone those using hydrogen peroxide and UV light alone or in combination with ozone.

The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

The invention claimed is:

1. A rack for use in the treatment of contaminated or potentially contaminated items, comprising:
    at least one stringer;
    at least two vertical grates spaced along said at least one stringer, wherein said at least two vertical grates each comprise an outer ring; an inner ring, at least two radial ring members connecting said outer ring to said inner ring; and at least one center connector interior of said inner ring and connected at two points on said inner ring, wherein the spacing between said grates is such that a respiratory mask can be placed between said grates; and at least one roller.

2. A rack for treatment of protective masks comprising a plurality of grates, two stringers, and at least one roller, each of said plurality of grates comprising an outer ring and a plurality of center connectors disposed along said outer ring and extending from said outer ring and connecting at the center of said outer ring, each grate being connected to both of said two stringers; wherein said grates are spaced along said stringers so as to accommodate at least one protective mask to rest securely between two of said plurality of grates; wherein said grates comprise a plurality of openings that allow gas to flow through said plurality of grates to contact said at least one protective mask.

3. The rack of claim 2 wherein said plurality of center connectors are disposed equidistant around said outer ring.

4. The rack of claim 2 wherein said at plurality of center connectors prevents each of said at least one protective mask from moving through said outer ring.

5. A rack for treatment of protective masks comprising two stringers, and at least one roller, and a plurality of grates spaced along said two stringers so as to accommodate at least one protective mask to rest securely between two of said plurality of grates; wherein said grates are circular in cross section and one of said stringers is located along the edge of said circular cross section of said grates; wherein said plurality of grates each further comprise at least two radial ring members, one outer ring, one inner ring, and at least two center connectors; wherein said radial ring members are disposed equidistant around said one outer ring and said one inner ring and said radial ring members connect said one outer ring and said one inner ring; and wherein said at least two center connectors prevent each of said at least one protective mask from moving through said inner ring.

* * * * *